(12) United States Patent
Li et al.

(10) Patent No.: US 9,054,320 B2
(45) Date of Patent: Jun. 9, 2015

(54) 1, 2, 4-TRIAZOLE-BASED DERIVATIVE, PRODUCTION PROCESS AND USE THEREOF, AND ORGANIC ELECTROLUMINESCENT DEVICE

(71) Applicants: BOE Technology Group Co., LTD., Beijing (CN); JiLin OLED Material Tech. Co., LTD., Changchun (CN)

(72) Inventors: Na Li, Beijing (CN); Yansong Li, Beijing (CN); Xiaoyu Ma, Beijing (CN); Hui Wang, Beijing (CN)

(73) Assignees: BOE Technology Group Co., Ltd., Beijing (CN); JiLin OLED Material Tech. Co., Ltd., Changchun (CN)

( * ) Notice: Subject to any disclaimer, the term of this patent is extended or adjusted under 35 U.S.C. 154(b) by 0 days.

(21) Appl. No.: 14/164,654

(22) Filed: Jan. 27, 2014

(65) Prior Publication Data
US 2014/0343293 A1 Nov. 20, 2014

(30) Foreign Application Priority Data
May 15, 2013 (CN) .......................... 2013 1 0179962

(51) Int. Cl.
*C07D 249/08* (2006.01)
*H01L 51/00* (2006.01)

(52) U.S. Cl.
CPC ........ *H01L 51/0058* (2013.01); *H01L 51/0052* (2013.01); *H01L 51/0061* (2013.01); *H01L 51/0067* (2013.01); *H01L 51/0072* (2013.01); *C07D 249/08* (2013.01)

(58) Field of Classification Search
CPC ...................................................... C07D 249/08
USPC ........................................................ 548/269.4
See application file for complete search history.

(56) References Cited

FOREIGN PATENT DOCUMENTS

EP          1013740 A2     6/2000

OTHER PUBLICATIONS

First Office action dated Feb. 8, 2014, for corresponding Chinese Patent application No. 201310179962.3 filed on May 15, 2013.

*Primary Examiner* — Shawquia Jackson
(74) *Attorney, Agent, or Firm* — Westman, Champlin & Koehler, P.A.

(57) ABSTRACT

The invention provides a 1,2,4-triazole-based derivative, a production process and use thereof, and an organic electroluminescent device. The invention belongs to the technical field of organic electroluminescence, and can give a blue light-emitting material having a higher luminescence efficiency. The 1,2,4-triazole-based derivative has a molecular structure of the following general formula, wherein A group represents an aromatic heterocyclic group having a carbon atom number of 8-18, a fused-ring aromatic group having a carbon atom number of 9-15, a fluorenyl group, or a triarylamino group. The 1,2,4-triazole-based derivative mentioned in the invention can be used in organic electroluminescent device.

14 Claims, 1 Drawing Sheet

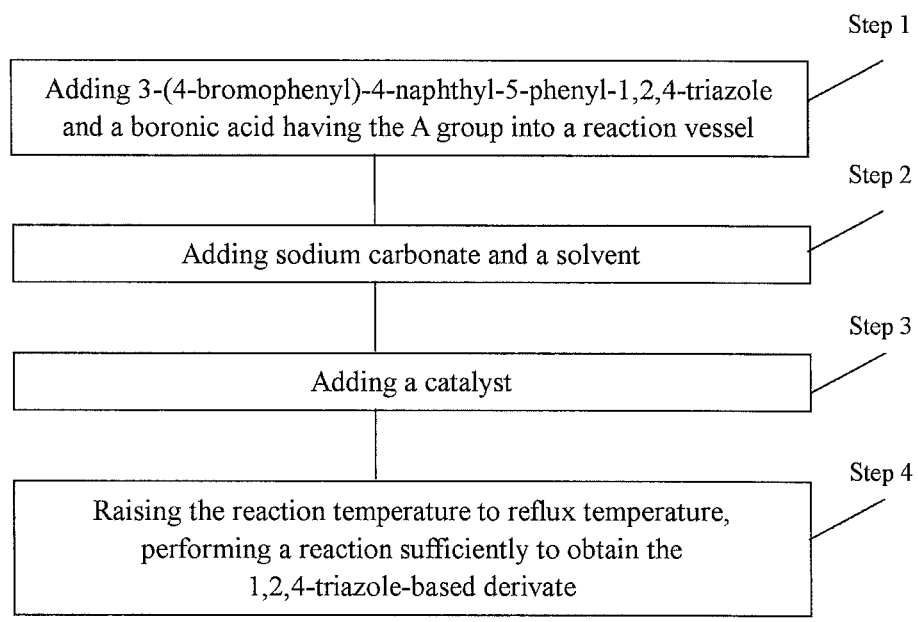

1,2,4-TRIAZOLE-BASED DERIVATIVE, PRODUCTION PROCESS AND USE THEREOF, AND ORGANIC ELECTROLUMINESCENT DEVICE

CROSS-REFERENCE TO RELATED APPLICATION

This Application is a non-provisional Application of Chinese Application No. CN 201310179962.3, filed May 15, 2013 in Chinese, the contents of which are hereby incorporated by reference in their entirety.

FIELD OF THE INVENTION

The invention relates to the technical field of organic electroluminescence, particularly, to a 1,2,4-triazole-based derivative, a production process and use thereof, and an organic electroluminescent device.

BACKGROUND OF THE INVENTION

The organic electroluminescence is a phenomenon that an organic material emits light by being excited by electric energy. The organic electroluminescence technology is considered as a new generation of the flat panel display technology due to its low driving voltage, wide viewing angle, low cost, high brightness, and capability to display in large area. Particularly, since 1987 when a low-voltage-driven small molecular light-emitting device was prepared by Tang, et al, the organic light-emitting diode has been developed greatly and brought into the industrialization progress.

One of the key technologies in the field of the organic light-emitting diode is the selection of the organic electroluminescent material. Currently, the organic electroluminescent material has been developed greatly in terms of polymers, metallic complexes, phosphorescent materials and fluorescent dyes, and luminescence in the three primary colors (i.e. red, blue and green) has been realized already. Here, the blue light-emitting material among the organic electroluminescent materials is one of the materials showing the three primary colors, which are used to realize the full color display. At the same time, for the red light-emitting and green light-emitting materials, the blue light-emitting material is also the host material for doping, because of the wider energy gap thereof. Additionally, the red light and green light can also be obtained from the blue light-emitting material by color conversion medium (CCM) technology so that the full color display is realized.

At present, the red light-emitting and green light-emitting materials for producing an organic electroluminescent device having good performances can substantially meet the requirement of the commercial application in practice due to their long life, high luminescence efficiency and stable performance. However, the blue light-emitting material prepared in prior art still has the problem that the luminescence efficiency is not high. Compared with the red light-emitting and green light-emitting materials, the development of the blue light-emitting material lags behind. Therefore, for the industrialization progress of the organic electroluminescent device, it is important to obtain a blue light-emitting material having a high luminescence efficiency.

SUMMARY OF THE INVENTION

In order to obtain a blue light-emitting material having a high luminescence efficiency, the invention provides a 1,2,4-triazole-based derivative, a production process and use thereof, and an organic electroluminescent device.

In order to achieve the object mentioned above, the invention adopts the following technical solutions.

A 1,2,4-triazole-based derivative having a molecular structure of the following general formula:

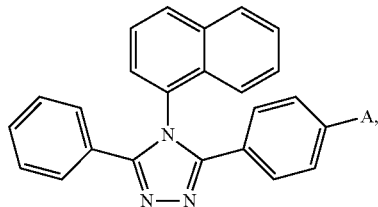

wherein A group represents an aromatic heterocyclic group having a carbon atom number of 8-18, a fused-ring aromatic group having a carbon atom number of 9-15, a fluorenyl group, or a triarylamino group.

Optionally, the A group is one selected from N-phenyl-3-carbazyl, triphenylamino, 2-naphthyl, 2-anthracyl, 9,9-dimethyl-2-fluorenyl and 2-pyrenyl.

A production process for the 1,2,4-triazole-based derivative provided in the invention, comprising the following steps of:

Step 1: adding 3-(4-bromophenyl)-4-naphthyl-5-phenyl-1,2,4-triazole and a boronic acid having the A group into a reaction vessel;

Step 2: adding sodium carbonate and a solvent;

Step 3: adding a catalyst;

Step 4: raising the reaction temperature to reflux temperature, performing a reaction sufficiently to obtain the 1,2,4-triazole-based derivative.

Optionally, 3-(4-bromophenyl)-4-naphthyl-5-phenyl-1,2,4-triazole and the boronic acid having the A group in Step 1 respectively have the following parts by mole of:

3-(4-bromophenyl)-4-naphthyl-5-phenyl-1,2,4-triazole: 1 part;

the boronic acid having the A group: 1.5-2.5 parts.

Optionally, sodium carbonate and 3-(4-bromophenyl)-4-naphthyl-5-phenyl-1,2,4-triazole in the Step 2 respectively have the following parts by mole of:

sodium carbonate: 3-4 parts;

3-(4-bromophenyl)-4-naphthyl-5-phenyl-1,2,4-triazole: 1 part.

Optionally, the solvent in the Step 2 is a mixed solvent of water and toluene at a volume ratio of 1:2.

Optionally, the catalyst and 3-(4-bromophenyl)-4-naphthyl-5-phenyl-1,2,4-triazole in Step 3 respectively have the following parts by mole of:

the catalyst: 1 part;

3-(4-bromophenyl)-4-naphthyl-5-phenyl-1,2,4-triazole: 50-100 parts.

Preferably, the reaction temperature in the Step 4 is 70-95° C.

Preferably, the reflux reaction time in the Step 4 is 24-30 hours.

Optionally, 3-(4-bromophenyl)-4-naphthyl-5-phenyl-1,2,4-triazole and the boronic acid having the A group in Step 1 respectively have the following parts by mole of:

3-(4-bromophenyl)-4-naphthyl-5-phenyl-1,2,4-triazole: 1 part;

the boronic acid having the A group: 1.5 parts;

the reaction time in Step 4 is 24 hours.

Use of the 1,2,4-triazole-based derivative provided in the invention in an organic electroluminescent device, wherein the 1,2,4-triazole-based derivative is used as an organic electroluminescent material, a luminescent host material, or a transporting material in the organic electroluminescent device.

An organic electroluminescent device comprising the 1,2,4-triazole-based derivative provided in the invention as a luminescent material, a luminescent host material, or a transporting material.

The invention provides a 1,2,4-triazole-based derivative, a production process and use thereof, and an organic electroluminescent device. Since the 1,2,4-triazole-based derivative has the strong electron withdrawing group A introduced thereto, it has a better ability for accepting electron, and therefore, it can transport electrons efficiently, which improves the luminescence efficiency of the 1,2,4-triazole-based luminescent material. Furthermore, the introduction of the A group also improve the solubility of the 1,2,4-triazole-based derivative, which allows it to be manufactured into a device more easily. Additionally, the position of the light-emission peak of the luminescent material can be adjusted by means of various transformations of aromatic substituents, so as to allow it to be used in the field of electroluminescence better.

BRIEF DESCRIPTION OF THE DRAWING

FIG. 1 is a flow chart of the production process for the 1,2,4-triazole-based derivative provided in the invention.

DETAILED DESCRIPTION OF THE INVENTION

The technical solutions in the examples of the invention are described clearly and fully below by referring to the drawings in the examples of the invention. Obviously, the examples described are only a part of the examples of the invention, but not all of them. All other examples, which are obtained by those skilled in the art on the basis of the examples in the invention on the premise that they do not pay an inventive labour, belong to the protection scope of the invention.

The 1,2,4-triazole-based derivative, the production process and use thereof, and the organic electroluminescent device according to the invention are described below by referring to the drawings in detail.

The invention provides a 1,2,4-triazole-based derivative having a molecular structure of the following general formula:

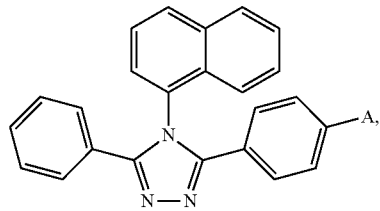

wherein A group represents an aromatic heterocyclic group having a carbon atom number of 8-18, a fused-ring aromatic group having a carbon atom number of 9-15, a fluorenyl group, or a triarylamino group.

The A group mentioned above belongs to aromatic compounds, has a π-conjugated plane and is a strong electron withdrawing group. By combined with other aromatic structure(s) in the general formula of the molecular structure, the A group can form a large conjugated plane, which has better ability for accepting electron. Additionally, the A group can also improve the solubility of the 1,2,4-triazole-based derivative.

Due to the introduction of the strong electron withdrawing group A, the 1,2,4-triazole-based derivative provided in the invention has a better ability for accepting electron, and therefore, it can transport electrons efficiently, thus the luminescence efficiency of the 1,2,4-triazole-based luminescent material is improved. Furthermore, the introduction of the A group also improves the solubility of the 1,2,4-triazole-based derivative, which allows it to be manufactured into a device more easily. Additionally, the position of the light-emission peak of the luminescent material can be adjusted by means of various transformations of aromatic substituents, so as to allow it to be used in the field of electroluminescence better.

Optionally, in other embodiments of the invention, the A group is one selected from N-phenyl-3-carbazyl, triphenylamino, 2-naphthyl, 2-anthracyl, 9,9-dimethyl-2-fluorenyl and 2-pyrenyl. Here, the 1,2,4-triazole-based derivatives having an above-mentioned groups are represented in order by the following molecular structural formulae 001, 002, 003, 004, 005, and 006.

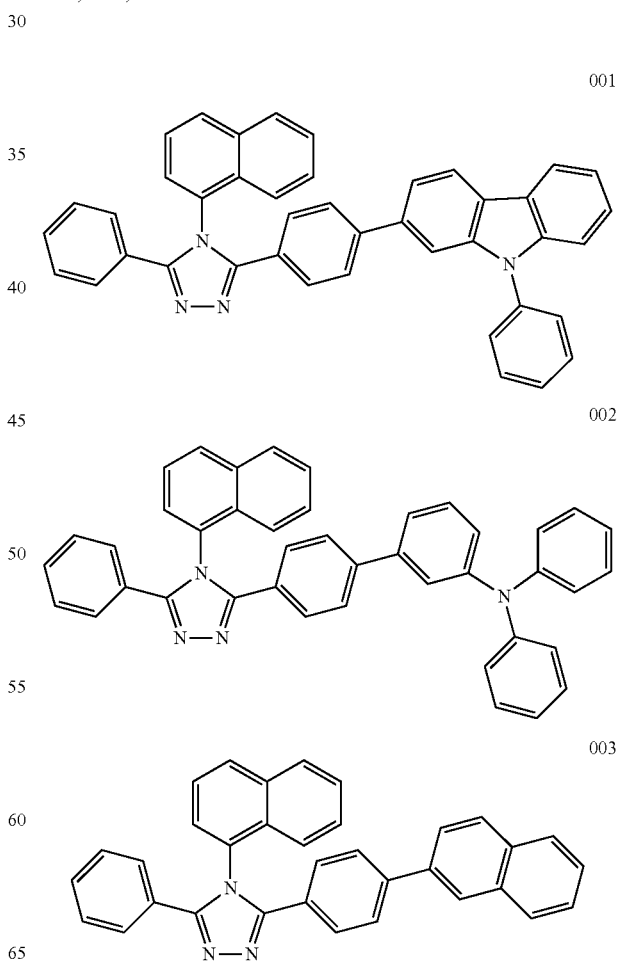

-continued

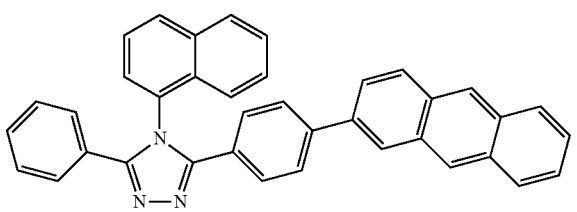

004

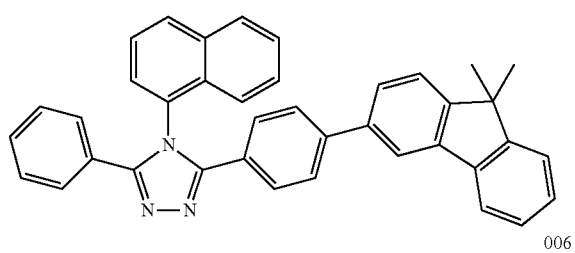

005

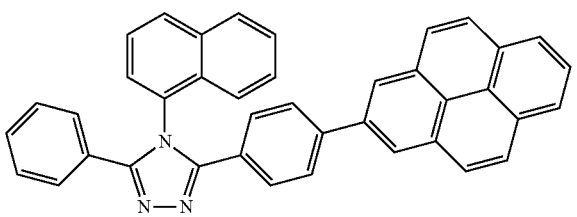

006

Corresponding to the above-mentioned 1,2,4-triazole-based derivative, the invention further provides a production process for the 1,2,4-triazole-based derivative. The reaction principle of the present process is Suzuki coupling reaction. Specifically, the invention comprises the following steps of:

Step 1: adding 3-(4-bromophenyl)-4-naphthyl-5-phenyl-1,2,4-triazole and a boronic acid having the A group into a reaction vessel. In the present step, reactants, i.e. 3-(4-bromophenyl)-4-naphthyl-5-phenyl-1,2,4-triazole and a boronic acid having the A group, are weighed in appropriate amount. Preferably, 3-(4-bromophenyl)-4-naphthyl-5-phenyl-1,2,4-triazole and the boronic acid having the A group in this step respectively have the following parts by mole of: 3-(4-bromophenyl)-4-naphthyl-5-phenyl-1,2,4-triazole: 1 part; the boronic acid having the A group: 1.5-2.5 parts. Further preferably, 3-(4-bromophenyl)-4-naphthyl-5-phenyl-1,2,4-triazole and the boronic acid having the A group in this step respectively have the following parts by mole of: 3-(4-bromophenyl)-4-naphthyl-5-phenyl-1,2,4-triazole: 1 part; the boronic acid having the A group: 1.5 part. It can be appreciated that the examples of the invention are not limited thereto and those skilled in the art can determine the parts by mole of the above-mentioned reactants according to the disclosure of the invention and the well-known general knowledge or the conventional technical means in the art.

It is should be indicated that in the present production process, all of the reactants, as well as the reactants, the solvent or the catalyst in the sequent steps are added under a condition of nitrogen protection. Firstly, people can evacuate the reaction environment, charge nitrogen gas, and add the reactants under nitrogen protection, so that the interference in the reaction from the oxygen in the reaction vessel is avoided. Secondly, the reactants, the solvent or the catalyst in the sequent steps are further added in the condition that nitrogen is kept charging, so that any stage in the operation is carried out in a nitrogen environment.

It can be appreciated that the process of nitrogen protection can also comprise performing the corresponding nitrogen protection after the addition of the reactants in Step 1, so as to ensure that the reactants, the solvent or the catalyst in the sequent steps are added under the nitrogen protection.

The invention is not limited thereto, and those skilled in the art can select other gases, which do not interfere in the reaction, according to the disclosure of the invention and the well-known general knowledge or the conventional technical means in the art.

Step 2: adding sodium carbonate and a solvent.

In the present step, sodium carbonate and a solvent are weighed in appropriate amount. Optionally, sodium carbonate and 3-(4-bromophenyl)-4-naphthyl-5-phenyl-1,2,4-triazole in this step respectively have the following parts by mole of: sodium carbonate: 3-4 parts; 3-(4-bromophenyl)-4-naphthyl-5-phenyl-1,2,4-triazole: 1 part. Preferably, sodium carbonate and 3-(4-bromophenyl)-4-naphthyl-5-phenyl-1,2,4-triazole in this step respectively have the following parts by mole of: sodium carbonate: 3 parts; 3-(4-bromophenyl)-4-naphthyl-5-phenyl-1,2,4-triazole: 1 part.

Optionally, the solvent in the present step is a mixed solvent of water and toluene, further optionally, a mixed solvent of water and toluene at a volume ratio of 1:2. It can be appreciated that the examples of the invention are not limited thereto and those skilled in the art can determine the parts by mole of the above-mentioned reactants and solvent according to the disclosure of the invention and the well-known general knowledge or the conventional technical means in the art.

Step 3: adding a catalyst.

Optionally, the catalyst in the present step can be tetrakis(triphenylphosphine) palladium. Further preferably, the catalyst and 3-(4-bromophenyl)-4-naphthyl-5-phenyl-1,2,4-triazole respectively have the following parts by mole of: the catalyst: 1 part; 3-(4-bromophenyl)-4-naphthyl-5-phenyl-1,2,4-triazole: 50-100 parts. It can be appreciated that the above mentioned is merely an illustrated description and those skilled in the art can also select other catalysts suitable for the Suzuki coupling reaction and determine the corresponding amount to be used.

Step 4: raising the reaction temperature to reflux temperature, sufficiently reacting to obtain the 1,2,4-triazole-based derivative.

Preferably, the reaction temperature in the Step 4 is 70-95° C. Further preferably, the reaction temperature in the Step 4 is 70° C.

Preferably, the reflux reaction time in the Step 4 is 24-30 hours. Further preferably, the reflux reaction time in the Step 4 is 24 hours.

It is should be indicated that the reaction product obtained in the present step is a crude product, which can be subjected to a further purification step, if necessary. Optionally, the purification steps include operations such as cooling, precipitation, vacuum filtration, washing the resultant filter cake with water, ethanol and diethyl ether, and then performing purification by column chromatography or the like, and thus a reaction product having higher purity can be obtained. Here, the solvent of the purification by column chromatography is preferably a mixed solvent of petroleum ether and ethyl acetate at a volume ratio of 1:8.

In the production process for 1,2,4-triazole-based derivative provided in the invention, the strong electron withdrawing group A is introduced by strictly controlling the conditions, such as reaction temperature, reaction time, and the like, and a blue light-emitting material having a higher luminescence efficiency is produced. In this process, the synthesis steps are simple, the cost of the solvents to be used is lower, and the derivative produced has high purity, and the yield can be 92% or more, which can meet the requirement of large scale industrialization.

Preferably, other embodiments of the invention provide a production process for a 1,2,4-triazole-based derivative.

3-(4-bromophenyl)-4-naphthyl-5-phenyl-1,2,4-triazole and the boronic acid having the A group in Step 1 respectively have the following parts by mole of: 3-(4-bromophenyl)-4-naphthyl-5-phenyl-1,2,4-triazole: 1 part; the boronic acid having the A group: 1.5 parts. The reaction time in the Step 4 is 24 hours.

The 1,2,4-triazole-based derivative prepared in the invention can exhibit a higher luminescence efficiency. The luminescence efficiency in solution can reach 97.8%, and after it is made into a thin film, the luminescence efficiency can reach 90.1%. Compared with prior art in which the maximal luminescence efficiency in a solution is 81.8%, and after it is made into a thin film, the maximal luminescence efficiency is 89%, it is a significant improvement.

Corresponding to the above-mentioned 1,2,4-triazole-based derivative, the invention also provides the use of the above-mentioned 1,2,4-triazole-based derivative in an organic electroluminescent device. The 1,2,4-triazole-based derivative is used in the organic electroluminescent device as an organic luminescent material, a luminescent host material, or a transporting material.

The 1,2,4-triazole-based derivative provided in the invention can be used in an electroluminescent device as an organic luminescent material, a luminescent host material, or a transporting material, and has a better quantum efficiency of electroluminescence and chemical stability. The organic luminescent materials made from this kind of derivative can be either coated directly on a surface of a device via evaporation, or dispersed in an inert polymer to perform a spin coating, or dispersed in a matrix of a light-emitting polymer for a synchronous processing, which greatly improves the feasibility of processing. Due to the introduction of the strong electron withdrawing group A, the 1,2,4-triazole-based derivative has a higher luminescence efficiency, and furthermore, improves the quality of the luminescence of the organic electroluminescent device.

Corresponding to the above-mentioned 1,2,4-triazole-based derivative, the invention also provides an organic electroluminescent device. The organic electroluminescent device comprises the 1,2,4-triazole-based derivative as a luminescent material, a luminescent host material, or a transporting material.

The blue light-emitting device using the 1,2,4-triazole-based derivative provided in the invention as the blue light-emitting material has a higher luminescence efficiency and good performances in terms of brightness and stability.

In order to describe the 1,2,4-triazole-based derivative, the production process and use thereof, and the organic electroluminescent device provided in the invention better, the detailed description is performed by referring to specific Examples. Examples 1-6 describes the synthesis processes and tests for performance of the compounds of the previous molecular structural formulae 001-006 in detail.

EXAMPLE 1

Synthesis of Compound 001

Under a nitrogen environment, 3-(4-bromophenyl)-4-naphthyl-5-phenyl-1,2,4-triazole (21.32 g, 50 mmol) and N-phenyl-3-carbazyl boronic acid (21.53 g, 75 mmol) were added into a three-necked flask equipped with a heating means, a refluxing means and a stirring means. Then sodium carbonate (15.90 g, 150 mmol), toluene (250 ml) and water (125 ml) were added. Finally, tetrakis(triphenylphosphine) palladium (0.57 g, 0.5 mmol) was added. The temperature was raised to 70° C., and the mixture was reacted for 24 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether:ethyl acetate=1:8). The mixed solvent was recovered. After drying, an off-white Compound 001 (27.37 g) was obtained, and the yield thereof was 93% or more.

The specific synthesis route for Compound 001 was as follows:

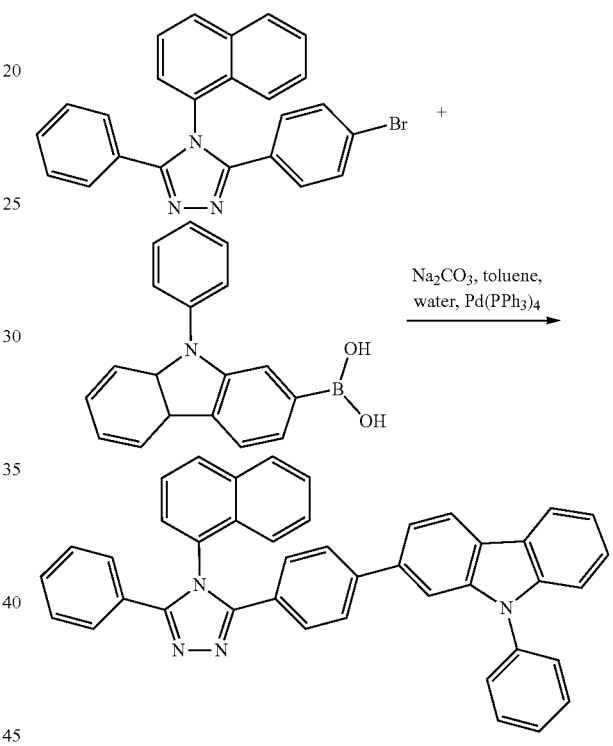

As the result of the analysis for Compound 001 by mass spectrography, the measured value of the molecular weight of the compound was 588.68, while the calculated one was 588.70.

As the result of the analysis for Compound 001 by an elemental analyzer, the measured values of each element in the compound were C:85.68%, H:4.80%, N:9.53%, while the calculated ones were C:85.69%, H:4.79%, N:9.52%.

EXAMPLE 2

Synthesis of Compound 002

Under a nitrogen environment, 3-(4-bromophenyl)-4-naphthyl-5-phenyl-1,2,4-triazole (21.32 g, 50 mmol) and 4-(4-triphenylamine)naphthyl boronic acid (31.52 g, 90 mmol) were added into a three-necked flask equipped with a heating means, a refluxing means and a stirring means. Then sodium carbonate (16.56 g, 160 mmol), toluene (250 ml) and water (125 ml) were added. Finally, tetrakis(triphenylphosphine)palladium (0.69 g, 0.6 mmol) was added. The temperature was raised to 75° C., and the mixture was reacted for 25 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether: ethyl acetate=1:8). The mixed solvent was recovered. After drying, an off-white Compound 002 (27.47 g) was obtained, and the yield thereof was 93% or more.

The specific synthesis route for Compound 002 was as follows:

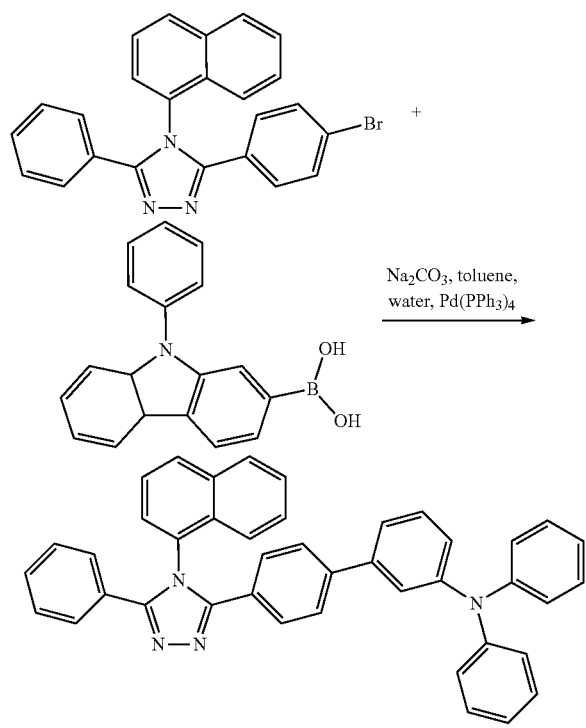

As the result of the analysis for Compound 002 by mass spectrography, the measured value of the molecular weight of the compound was 590.71, while the calculated one was 590.70.

As the result of the analysis for Compound 002 by an elemental analyzer, the measured values of each element in the compound were C:85.40%, H:5.12%, N:9.48%, while the measured ones were C:85.41%, H:5.10%, N:9.49%.

EXAMPLE 3

Synthesis of Compound 003

Under a nitrogen environment, 3-(4-bromophenyl)-4-naphthyl-5-phenyl-1,2,4-triazole (21.32 g, 50 mmol) and 10-(2-naphthyl)anthracyl boronic acid (40.40 g, 115 mmol) were added into a three-necked flask equipped with a heating means, a refluxing means and a stirring means. Then sodium carbonate (25.4 g, 190 mmol), toluene (250 ml) and water (125 ml) were added. Finally, tetrakis(triphenylphosphine) palladium (0.45 g, 0.9 mmol) was added. The temperature was raised to 80° C., and the mixture was reacted for 28 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether:ethyl acetate 1:8). The mixed solvent was recovered. After drying, an off-white Compound 003 (22.26 g) was obtained, and the yield thereof was 94% or more.

The specific synthesis route for Compound 003 was as follows:

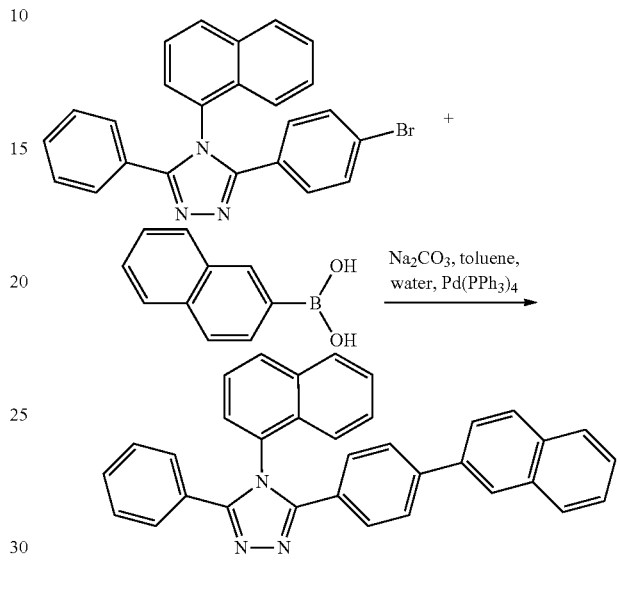

As the result of the analysis for Compound 003 by mass spectrography, the calculated value of the molecular weight of the compound was 473.57, while the measured one was 473.59.

As the result of the analysis for Compound 003 by an elemental analyzer, the calculated values of each element in the compound were C:86.23%, H:4.90%, N:8.87%, while the measured ones were C:86.25%, H:4.89%, N:8.86%.

EXAMPLE 4

Synthesis of Compound 004

Under a nitrogen environment, 3-(4-bromophenyl)-4-naphthyl-5-phenyl-1,2,4-triazole (21.32 g, 50 mmol) and 10-(2-anthracyl)-anthracyl boronic acid (41.80 g, 105 mmol) were added into a three-necked flask equipped with a heating means, a refluxing means and a stirring means. Then sodium carbonate (19.08 g, 180 mmol), toluene (250 ml) and water (125 ml) were added. Finally, tetrakis(triphenylphosphine) palladium (0.92 g, 0.8 mmol) was added. The temperature was raised to 85° C., and the mixture was reacted for 27 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether:ethyl acetate=1:8). The mixed solvent was recovered. After drying, an off-white Compound 004 (24.09 g) was obtained, and the yield thereof was 92% or more.

The specific synthesis route for Compound 004 was as follows:

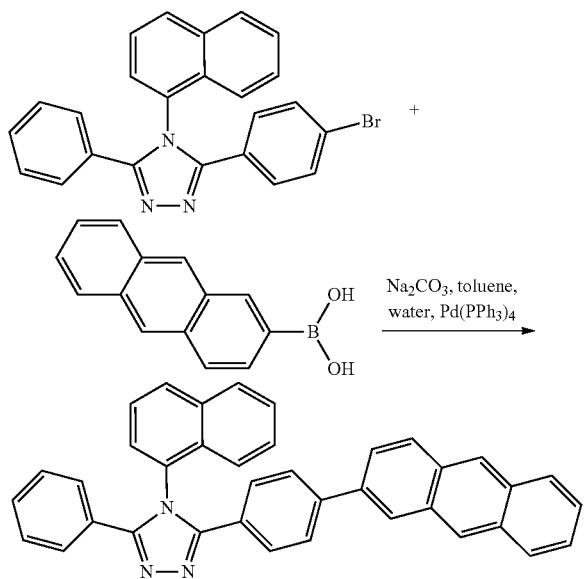

As the result of the analysis for Compound 004 by mass spectrography, the calculated value of the molecular weight of the compound was 523.63, while the measured one was 523.61.

As the result of the analysis for Compound 004 by an elemental analyzer, the calculated values of each element in the compound were C:87.16%, H:4.81%, N:8.02%, while the measured ones were C:87.15%, H:4.80%, N:8.04%.

EXAMPLE 5

Synthesis of Compound 005

Under a nitrogen environment, 3-(4-bromophenyl)-4-naphthyl-5-phenyl-1,2,4-triazole (21.32 g, 50 mmol) and 4-(9,9-dimethylfluoren-2-yl)-phenyl boronic acid (39.36 g, 125 mmol) were added into a three-necked flask equipped with a heating means, a refluxing means and a stirring means. Then sodium carbonate (21.20 g, 200 mmol), toluene (250 ml) and water (125 ml) were added. Finally, tetrakis(triphenylphosphine)palladium (1.15 g, 1.0 mmol) was added. The temperature was raised to 90° C., and the mixture was reacted for 30 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether:ethyl acetate=1:8). The mixed solvent was recovered. After drying, an off-white Compound 005 (25.36 g) was obtained, and the yield thereof was 94% or more.

The specific synthesis route for Compound 005 was as follows:

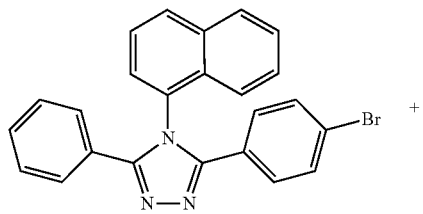

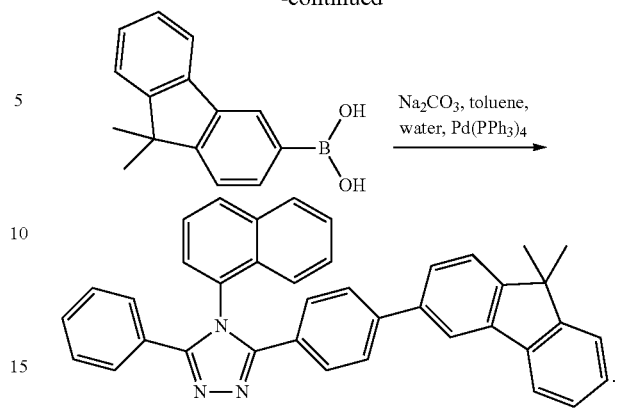

As the result of the analysis for Compound 005 by mass spectrography, the calculated value of the molecular weight of the compound was 539.67, while the measured one was 539.65.

As the result of the analysis for Compound 005 by an elemental analyzer, the calculated values of each element in the compound were C:86.80%, H:5.42%, N:7.79%, while the measured ones were C:86.78%, H:5.43%, N:7.78%.

EXAMPLE 6

Synthesis of Compound 006

Under a nitrogen environment, 3-(4-bromophenyl)-4-naphthyl-5-phenyl-1,2,4-triazole (21.32 g, 50 mmol) and 2-pyrenyl boronic acid (24.61 g, 100 mmol) were added into a three-necked flask equipped with a heating means, a refluxing means and a stirring means. Then sodium carbonate (18.02 g, 170 mmol), toluene (250 ml) and water (125 ml) were added. Finally, tetrakis(triphenylphosphine)palladium (0.80 g, 0.7 mmol) was added. The temperature was raised to 95° C., and the mixture was reacted for 26 hours while refluxing. After the mixture was cooled to the room temperature and a solid was precipitated, vacuum filtration was carried out. After the resultant filter cake was washed with water, ethanol and diethyl ether in this order, it was purified by column chromatography (petroleum ether:ethyl acetate=1:8). The mixed solvent was recovered. After drying, an off-white Compound 006 (25.19 g) was obtained, and the yield thereof was 92% or more.

The specific synthesis route for Compound 006 was as follows:

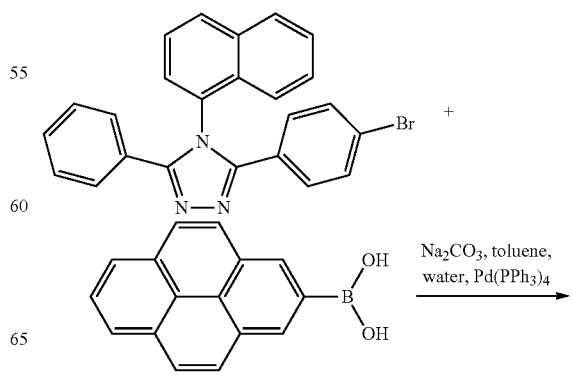

-continued

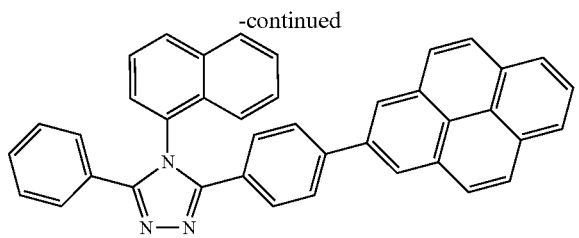

As the result of the analysis for Compound 006 by mass spectrography, the calculated value of the molecular weight of the compound was 547.65, while the measured one was 547.68.

As the result of the analysis for Compound 006 by an elemental analyzer, the calculated values of each element in the compound were C:87.73%, H:4.60%, N:7.67%, while the measured ones were C:87.71%, H:4.62%, N:7.68%.

Tests for Performances
(1) Test for Purity

The Compounds 001-006 were subjected to the test for purity by high performance liquid chromatography (HLPC). The results are listed in Table 1.

(2) Test for Luminescence Efficiency

The samples were formulated into diluted solutions having a concentration of $1\times10^{-6}$ mol/L, respectively. The solutions were made into thin films via spin coating method and the luminescence efficiencies of the above-mentioned diluted solutions and thin films were measured respectively by Edinburdh-FLS920 (steady state/transient state fluorescence spectrometer). The specific data are shown in table 1.

TABLE 1

Luminescence Efficiencies of the Compounds 001-006 obtained in the Examples

| Sample | Luminescence Efficiency in Diluted Solution | Luminescence Efficiency in Thin Film | HLPC Purity |
|---|---|---|---|
| Compound 001 | 97.8% | 90.1% | >98% |
| Compound 002 | 96.7% | 89.4% | >98% |
| Compound 003 | 94.4% | 88.2% | >98% |
| Compound 004 | 95.2% | 89.6% | >98% |
| Compound 005 | 93.3% | 88.1% | >98% |
| Compound 006 | 97.1% | 88.5% | >98% |

In the reports on the study of synthesis for organic electroluminescent materials in the art, the luminescence efficiency of a synthesized organic electroluminescent material in diluted solution can reach 81.8% at most, and that in thin film ranges generally from 29% -89%. However, the 1,2,4-triazole-based derivative provided in the invention has a higher luminescence efficiency. As shown in table 1, each of the 1,2,4-triazole-based derivatives in Example 1-6 has a luminescence efficiency in diluted solution of 93% or more, which is much higher than 81.8% in prior art. Each luminescence efficiency in thin film is 88% or more and can reach 90.1% at most, which is higher than 89% in prior art. The high luminescence efficiency indicates that the 1,2,4-triazole-based derivative absolutely can be used in an electroluminescent device as a luminescent material, a luminescent host material, and a transporting material.

Obviously, the above-mentioned Examples are merely examples provided for a clear illustration, and not the limitation of the embodiments. Changes or modifications in other different forms can be made by those skilled in the art on the basis of the previous description. It is unnecessary and impossible to list all of the embodiments one by one herein. The changes and modification derived herefrom are also in the protection scope of the invention.

What is claimed is:

1. A 1,2,4-triazole-based derivative represented by the formula:

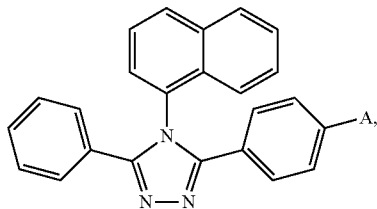

wherein A group represents an aromatic heterocyclic group having a carbon atom number of 8-18, a fused-ring aromatic group having a carbon atom number of 9-15, a fluorenyl group, or a triarylamino group.

2. The 1,2,4-triazole-based derivative according to claim 1, wherein the A group is one selected from N-phenyl-3-carbazyl, triphenylamino, 2-naphthyl, 2-anthracyl, 9,9-dimethyl-2-fluorenyl and 2-pyrenyl.

3. A production process for the 1,2,4-triazole-based derivative according to claim 1, comprising the following steps of:

Step 1: adding 3-(4-bromophenyl)-4-naphthyl-5-phenyl-1,2,4-triazole and a boronic acid having the A group into a reaction vessel;

Step 2: adding sodium carbonate and a solvent;

Step 3: adding a catalyst;

Step 4: raising the reaction temperature to reflux temperature, performing a reaction sufficiently to obtain the 1,2,4-triazole-based derivative.

4. The production process according to claim 3, wherein 3-(4-bromophenyl)-4-naphthyl-5-phenyl-1,2,4-triazole and the boronic acid having the A group in Step 1 respectively have the following parts by mole of:

3-(4-bromophenyl)-4-naphthyl-5-phenyl-1,2,4-triazole: 1 part;

the boronic acid having the A group: 1.5-2.5 parts.

5. The production process according to claim 3, wherein sodium carbonate and 3-(4-bromophenyl)-4-naphthyl-5-phenyl-1,2,4-triazole in the Step 2 respectively have the following parts by mole of:

sodium carbonate : 3-4 parts;

3-(4-bromophenyl)-4-naphthyl-5-phenyl-1,2,4-triazole: 1 part.

6. The production process according to claim 3, wherein the solvent in Step 2 is a mixed solvent of water and toluene at a volume ratio of 1:2.

7. The production process according to claim 3, wherein the catalyst and 3-(4-bromophenyl)-4-naphthyl-5-phenyl-1,2,4-triazole in Step 3 respectively have the following parts by mole of:

the catalyst: 1 part;

3-(4-bromophenyl)-4-naphthyl-5-phenyl-1,2,4-triazole: 50-100 parts.

8. The production process according to claim 3, wherein the reaction temperature in the Step 4 is 70-95° C.

9. The production process according to claim 3, wherein the reflux reaction time in the Step 4 is 24-30 hours.

10. The production process according to claim 3, wherein:
3-(4-bromophenyl)-4-naphthyl-5-phenyl-1,2,4-triazole and the boronic acid having the A group in Step 1 respectively have the following parts by mole of:
3-(4-bromophenyl)-4-naphthyl-5-phenyl-1,2,4-triazole: 1 part;
the boronic acid having the A group: 1.5 parts;
and the reaction time in the Step 4 is 24 hours.

11. A method of preparing an organic electroluminescent device by using the 1,2,4-triazole-based derivative according to claim 1, wherein the 1,2,4-triazole-based derivative is used as an organic luminescent material, a luminescent host material, or a transporting material in the organic electroluminescent device.

12. The method of preparing an organic electroluminescent device according to claim 11, wherein the A group is one selected from N-phenyl-3-carbazyl, triphenylamino, 2-naphthyl, 2-anthracyl, 9,9-dimethyl-2-fluorenyl and 2-pyrenyl.

13. An organic electroluminescent device comprising the 1,2,4-triazole-based derivative according to claim 1 as a luminescent material, a luminescent host material, or a transporting material.

14. The organic electroluminescent device according to claim 13, wherein the A group is one selected from N-phenyl-3-carbazyl, triphenylamino, 2-naphthyl, 2-anthracyl, 9,9-dimethyl-2-fluorenyl and 2-pyrenyl.

* * * * *